United States Patent [19]

Papenfuhs et al.

[11] 4,137,272

[45] Jan. 30, 1979

[54] PROCESS FOR THE MANUFACTURE OF 2-ALKOXY-6-BROMO-NAPHTHALENES

[75] Inventors: Theodor Papenfuhs, Frankfurt am Main; Kurt Gengnagel, Offenbach am Main, both of Fed. Rep. of Germany

[73] Assignee: Hoechst Aktiengesellschaft, Frankfurt am Main, Fed. Rep. of Germany

[21] Appl. No.: 791,854

[22] Filed: Apr. 28, 1977

[30] Foreign Application Priority Data

May 4, 1976 [DE] Fed. Rep. of Germany ....... 2619641

[51] Int. Cl.$^2$ ............................................. C07C 41/10
[52] U.S. Cl. ................................... 568/628; 568/737; 568/634; 562/467
[58] Field of Search ........... 260/520 D, 623 R, 612 D

[56] References Cited

U.S. PATENT DOCUMENTS 2,488,472  11/1949  Kremers ................... 260/623 R UX Primary Examiner—Bernard Helfin
Attorney, Agent, or Firm—Connolly and Hutz

[57] ABSTRACT

A new process, which can be carried out on the technical scale, had been found for the preparation of 2-alkoxy-6-bromo-naphthalenes, especially suitable as starting compounds for the synthesis of estrogens, which comprises brominating 2-hydroxy-naphthalene-1-carboxylic acid with bromine, decarboxylating the 6-bromo-2-hydroxynaphthalene-1-carboxylic acid by heating the reaction mixture at 100–125° C., and alkylating the 6-bromo-2-hydroxy-naphthalene formed. The process can be conducted easily and with high yields.

1 Claim, No Drawings

PROCESS FOR THE MANUFACTURE OF 2-ALKOXY-6-BROMO-NAPHTHALENES

The present invention is concerned with an improved process for the production of 2-alkoxy-6-bromo-naphthalenes, preferably having an alkoxy group of 1–4 carbon atoms, and especially 2-methoxy- or 2-ethoxy-6-bromo-naphthalene.

2-Alkoxy-6-bromo-naphthalenes, especially 2-methoxy-6-bromo-naphthalene, are important starting compounds for the production of pharmaceutical products, especially synthetic estrogens, such as methallenestril (see The Merck Index, 8th Edition, (1968), page 669). For the production of 2-methoxy-6-bromo-naphthalene, 2-hydroxy-naphthalene-1-carboxylic acid was converted with diazomethane into 2-methoxy-naphthalene-1-carboxylic acid methyl ester, the latter was brominated with bromine in acetic acid to form 6-bromo-2-methoxy-naphthalene-1-carboxylic acid methyl ester, then the carboxylic acid methyl ester group was hydrolyzed, and the resulting 6-bromo-2-methoxy-naphthalene-1-carboxylic acid was decarboxylated to form 2-methoxy-6-bromo-naphthalene (see J. Chem. Soc. 1941, 687 + 688).

This process has numerous disadvantages, so that it cannot be considered for industrial use. Thus, for example, methylation with diazomethane is not industrially possible. For the bromination one mol of bromine in acetic acid is used, and the decarboxylation of 2-methoxy-6-bromo-naphthalene-1-carboxylic acid does not take place in a unitary manner. Furthermore, the total yield of the process is unsatisfactory.

It has now been found that the production of 2-alkoxy-6-bromo-naphthalenes can be simplified and the yields appreciably improved by brominating 2-hydroxy-naphthalene-1-carboxylic acid with bromine to form 6-bromo-2-hydroxy-naphthalene-1-carboxylic acid, then splitting off the carboxylic acid group by heating the reaction mixture at a temperature of 100° to 125° C., and preferably of about 105° to 120° C., and especially of about 105° to 115° C., and alkylating the 6-bromo-2-hydroxy-naphthalene (alkylation may occur in analogous manner to known alkylation processes).

The process takes place in accordance with the following reaction scheme:

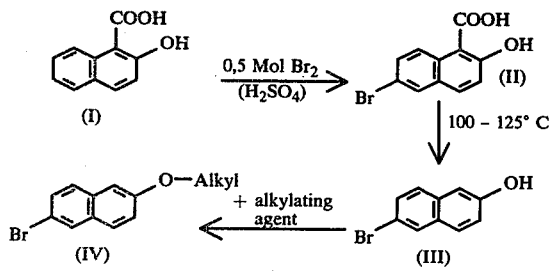

The compound (II) is new.

The process is advantageously carried out by brominating 2-hydroxy-naphthalene-1-carboxylic acid, especially advantageously by treatment with bromine in sulfuric acid, preferably in sulfuric acid of 90–98% strength, such as about 94–96% strength, and at about 5°–30° C., especially at 15°–25° C., 0.5 mol of bromine being used per mol of 2-hydroxy-naphthalene-1-carboxylic acid, and then heating the bromination mixture at 105°–120° C., whereby decarboxylation takes place with the formation of 6-bromo-2-hydroxy-naphthalene. The 6-bromo-2-hydroxy-naphthalene that precipitates is filtered off with suction and alkylated in an aqueous medium; for preparing the methyl ether or ethyl there is advantageously used dimethyl sulfate or diethyl sulfate. For preparing higher alkyl ethers there may also be used alkyl halides, especially bromides. The alkylation is carried out in a manner analogous to the known processes familiar to the expert.

The 6-bromo-2-alkoxy-naphthalenes precipitate from the aqueous alkylation mixture in solid form and can be isolated by filtering off with suction. They are obtained in a good yield and state of purity.

The 6-bromo-2-hydroxy-naphthalene-1-carboxylic acid obtained as intermediate product may, if desired, be isolated from the bromination mixture.

The following Examples illustrate the invention.

EXAMPLE 1

100 Grams of 2-hydroxy-1-naphthoic acid are introduced in the course of about 20 to 30 minutes into 800 grams of sulfuric acid of 95.5% strength at 18°–20° C. with external cooling. The mixture is then stirred for 30 minutes at that temperature, and dissolution occurs. In the course of 2 hours 45 grams of bromine are steadily added dropwise with weak external cooling at an internal temperature of 18°–20° C. The mixture is then stirred for 2 hours at this temperature, the red-brown bromine vapour disappearing also in the gas space.

Then the mixture is poured into 900 ml of water at 65°–70° C. to which 3 grams of an anionic dispersing agent are added, whereupon the temperature rises to 90°–95° C.

For the decarboxylation the mixture is heated at a temperature of 109°–111° C. for about 16 hours. From the initially practically colorless suspension of 6-bromo-2-hydroxy-1-naphthoic acid there forms after about 6 hours 6-bromo-2-hydroxy-naphthalene, which precipitates as an oil and, while stirring, solidifies upon cooling to form granules.

The mixture is cooled to 15°–20° C., stirred at this temperature for one hour, filtered off with suction, dried well with suction, washed with 3000 ml of water and dried with suction.

After drying at 60° C., 101 grams of 6-bromo-2-hydroxy-naphthalene are obtained which corresponds to a yield of 85.2% of theory.

100 Grams of 6-bromo-2-hydroxy-naphthalene are introduced into 600 ml of water. After the addition of 65 grams of an aqueous 33% sodium hydroxide solution, 5 grams of activated carbon and 5 grams of kieselguhr, the mixture is stirred for 30 minutes at 20°–25° C. The mixture is then filtered, the filter residue is washed with 100 ml of water, and the clear filtrate is introduced into the methylating vessel. In the course of 3 hours there are steadily added dropwise, starting at a pH-value of 13.5, 80 grams of dimethyl sulfate at a temperature of 20°–25° C., and the precipitation of 6-bromo-2-methoxy-naphthalene sets in immediately. During the dropwise addition of the dimethyl sulfate the pH-value falls to about 12. The mixture is then stirred for one hour at 20°–25° C., during which the pH-value is maintained at 12–13 by the dropwise addition of about 25 grams of aqueous 33% sodium hydroxide solution.

The precipitated product is then filtered off with suction, dried with suction, washed neutral with 2500 ml of water, again dried well with suction, and dried at 60° C. in an air-circulation cabinet. 94 Grams of 6-bromo-2-methoxy-naphthalene are obtained corresponding to a yield of 88.4% of theory.

By using diethyl sulfate for the alkylation, instead of dimethyl sulfate, 6-bromo-2-ethoxy-naphthalene is obtained in a yield of 86% of theory.

EXAMPLE 2

Bromination is carried out according to the data given in Example 1. The bromination mixture so obtained is poured into water, the precipitate is filtered off and dried.

6-Bromo-2-hydroxy-naphthalene carboxylic acid is obtained in the form of a white crystalline powder. The compound melts at 178°–180° C. (with decomposition).

Analysis: Br calc. 29.9%; found 29.3%.

What is claimed is:

1. A process for the manufacture of 2-alkoxy-6-bromo-naphthalene having 1 or 2 carbons in the alkoxy group, which comprises brominating 1 mol of 2-hydroxy-naphthalene-1-carboxylic acid with 0.5 mol of bromine in sulfuric acid at about 5° to 30° C., heating the bromination mixture of 105°–120° C., isolating the formed and precipitated 6-bromo-2-hydroxy-naphthalene and alkylating it with dimethylsulfate or diethylsulfate in aqueous medium.

* * * * *